United States Patent
Musio et al.

(10) Patent No.: US 12,139,453 B2
(45) Date of Patent: Nov. 12, 2024

(54) PROCESS FOR THE PREPARATION OF PERHALOACYL PEROXIDES

(71) Applicant: SOLVAY SPECIALTY POLYMERS ITALY S.P.A., Bollate (IT)

(72) Inventors: Stefana Musio, Saronno (IT); Ivan Diego Wlassics, Garessio (IT); Serena Carella, Parabiago (IT); Marco Avataneo, Milan (IT)

(73) Assignee: SOLVAY SPECIALTY POLYMERS ITALY S.P.A., Bollate (IT)

( * ) Notice: Subject to any disclaimer, the term of this patent is extended or adjusted under 35 U.S.C. 154(b) by 628 days.

(21) Appl. No.: 17/311,033

(22) PCT Filed: Dec. 19, 2019

(86) PCT No.: PCT/EP2019/086194
§ 371 (c)(1),
(2) Date: Jun. 4, 2021

(87) PCT Pub. No.: WO2020/127654
PCT Pub. Date: Jun. 25, 2020

(65) Prior Publication Data
US 2022/0024867 A1 Jan. 27, 2022

(30) Foreign Application Priority Data
Dec. 20, 2018 (EP) .................... 18214305

(51) Int. Cl.
*C07C 407/00* (2006.01)
*C08F 4/34* (2006.01)
*C08F 110/02* (2006.01)
*C08F 114/18* (2006.01)

(52) U.S. Cl.
CPC ............ *C07C 407/003* (2013.01); *C08F 4/34* (2013.01); *C08F 110/02* (2013.01); *C08F 114/185* (2013.01)

(58) Field of Classification Search
USPC ............................. 526/209, 231; 252/182.15
See application file for complete search history.

(56) References Cited

U.S. PATENT DOCUMENTS

| | | | |
|---|---|---|---|
| 2,580,358 A | 12/1951 | Miller et al. | |
| 2,580,373 A | 12/1951 | Zimmerman | |
| 2,700,662 A * | 1/1955 | Young | C08F 14/24 |
| | | | 568/560 |
| 2,816,147 A | 12/1957 | Weber et al. | |
| 3,624,250 A | 11/1971 | Carlson | |
| 3,847,881 A | 11/1974 | Mueller et al. | |
| 4,513,129 A | 4/1985 | Nakagawa et al. | |
| 5,182,342 A | 1/1993 | Feiring et al. | |
| 5,831,131 A | 11/1998 | Krespan et al. | |
| 2002/0026011 A1 * | 2/2002 | Brothers | C07C 407/00 |
| | | | 525/107 |
| 2008/0039599 A1 | 2/2008 | Du et al. | |
| 2012/0022286 A1 | 1/2012 | Ueno et al. | |

FOREIGN PATENT DOCUMENTS

| | | | | |
|---|---|---|---|---|
| CN | 102369184 A | 3/2012 | | |
| EP | 0612767 A1 | 8/1994 | | |
| EP | 0673951 A1 | 9/1995 | | |
| EP | 0673952 A1 | 9/1995 | | |
| EP | 1238988 A1 * | 9/2002 | ................ | C08F 4/34 |
| GB | 794830 A | 5/1958 | | |
| JP | 2006089472 A | 4/2006 | | |
| TW | 201235342 A | 9/2012 | | |
| WO | 2008019155 A1 | 2/2008 | | |

OTHER PUBLICATIONS

Trichloroacetyl chloride Product Specification document, Glentham Life Sciences, Ltd., 2023 (single page). (Year: 2023).*
Shen Yulong et al.; "Green Chemistry;" China Environmental Press; Apr. 30, 2016; pp. 1-7, 183-186 (11 pages).
Office Action issued in Chinese Application No. 201980087749.5 mailed on Apr. 29, 2023 (10 pages).
Search Report issued in Chinese Application No. 201980087749.5, mailed on Apr. 29, 2023 (3 pages).
Chu Q. et al., "New fluorous/organic biphasic systems achieved by solvent tuning", Tetrahedron, 2007, vol. 63 No. 39, p. 9890-9895, Elsevier Science Publishers, Amsterdam, NL.

* cited by examiner

*Primary Examiner* — Fred M Teskin
(74) *Attorney, Agent, or Firm* — Osha Bergman Watanabe & Burton LLP

(57) ABSTRACT

A process for the preparation of perhaloacyl peroxides from perhaloacyl halides which is performed in the presence of a hydrofluoroether as the solvent.

10 Claims, No Drawings

PROCESS FOR THE PREPARATION OF PERHALOACYL PEROXIDES

This application claims priority to EP application 18214305.7 filed on 20 Dec. 2018, the whole content of this application being incorporated herein by reference for all purposes.

TECHNICAL FIELD

The invention relates to a process for the preparation of perhaloacyl peroxides, in particular for the preparation of bis(trichloroacetyl) peroxide, and to their use as initiators in the polymerization of halogenated monomers.

BACKGROUND ART

This application is a U.S. national stage entry under 35 U.S.C. § 371 of International Application No. PCT/EP2019/086194 filed Dec. 19, 2019, which claims priority to European application No. 18214305.7, filed on Dec. 20, 2018. The entire contents of these applications are explicitly incorporated herein by this reference.

Perhaloacyl peroxides, such bis(trichloroacetyl) peroxide, are useful as polymerization initiators in particular in the polymerization of halogenated monomers, such as chlorotrifluoroethylene and tetrafluoroethylene. The absence of any hydrogen atom in these peroxides allows the preparation of halogenated polymers having fully halogenated chain ends and thus provided with exceptional stability.

Processes for the preparation of perhaloacyl peroxides, such as bis(trichloroacetyl) peroxide, are known. For instance, U.S. Pat. No. 2,580,373 discloses a process for preparing perhaloacetyl peroxides which comprises reacting an alkali metal or alkaline earth metal peroxide in an aqueous brine solution with a perhalo derivative of acetic acid and recovering the solid perhaloacetyl peroxide from the aqueous system as a solid. U.S. Pat. No. 2,816,147 discloses a continuous process for the preparation of perhaloacetyl peroxides which comprises contacting a mixture of an inorganic peroxide and a brine solution with a mixture of perhalogenated acetyl halide and a halogenated hydrocarbon and continuously recovering a mixture of the perhaloacetyl peroxide in the halogenated hydrocarbon as the product of the process. The halogenated hydrocarbons disclosed in U.S. Pat. No. 2,816,147 are trichlorofluoromethane, trichlorotrifluoroethane, carbon tetrachloride, chloroform and dichlorofluoromethane.

Solutions of the perhaloacetyl peroxide, notably of bis(trichloroacetyl) peroxide, in halogenated hydrocarbons such as those disclosed in U.S. Pat. No. 2,816,147 have been used without further purification to initiate the polymerization reaction of halogenated monomers.

In particular, solutions of bis(trichloroacetyl) peroxide in trichlorotrifluoroethane, in particular 1,1,2-trichloro-1,2,2-trifluoroethane, have been used in the preparation of polymers comprising chlorotrifluoroethylene, for instance in U.S. Pat. No. 3,847,881.

Halogenated hydrocarbons such as those disclosed in U.S. Pat. No. 2,816,147, e.g. trichlorotrifluoroethane, have a high potential for destroying ozone in the stratosphere and their production and use has been severely limited by the Montreal Protocol. On the other hand, perfluorocarbons are so-called greenhouse gases and may cause global warming. They are thus not suitable for the replacement of trichlorotrifluoroethane.

The need thus exists to provide solutions of perhaloacyl peroxides, e.g. bis(trichloroacetyl) peroxide, in solvents which do not have a high potential to deplete ozone or cause global warming and which can be used in the polymerization of halogenated monomers without adversely affect the properties of the polymer obtained. The solvent should have low telegenic activity, low or no flammability and low miscibility with water.

SUMMARY OF INVENTION

It has now been found that a suitable class of solvents for the preparation and subsequent use of perhaloacyl peroxides, e.g. bis(trichloroacetyl) peroxide, is represented by certain hydrofluoroethers.

A first object of the present invention is thus a process for the preparation of a perhaloacyl peroxide said process comprising:
- contacting an aqueous phase comprising an inorganic peroxide with a mixture of a perhaloacyl halide and a hydrofluoroether,
- allowing the inorganic peroxide to react with the perhaloacyl halide to obtain a perhaloacyl peroxide, and
- separating the aqueous phase from a mixture comprising the perhaloacyl peroxide and the hydrofluoroether.

The term "hydrofluoroether" is used herein to refer to organic compounds comprising one or more ether oxygen atoms and only C, H and F atoms.

Notable, non-limiting examples of hydrofluoroethers are those that comply with formula (IA) or (IB) here below:

$$R\text{—}O\text{—}R' \quad (IA)$$

$$RO\text{-}J\text{-}(O)_j\text{—}R' \quad (IB)$$

wherein:
R and R', equal or different from each other, are independently selected from the group consisting of linear or branched   $F_{2u-u'}H_{u'}OC_yF_{2y+1}$ groups; m, n, u, w, y, z are integers from 1 to 10, preferably from 1 to 8; h, u' and w' are integers ≥1, chosen so that h≤2n+1, u'≤2u, w'≤2w+1;
j is equal to 0 or 1; and
J is a divalent hydrocarbon radical having 1 to 12 carbon atoms, linear or branched, aliphatic or aromatic, preferably an aliphatic divalent hydrocarbon group having 1 to 6 carbon atoms, e.g. —CH$_2$—, —CH$_2$CH$_2$— or —CH(CH$_3$)—.

Mixtures of hydrofluoroethers as defined above may also be used.

Advantageously, the hydrofluoroether is selected among the hydrofluoroethers of formula (IA) or (IB) as defined above which satisfy the following features:
- have a boiling point in the range from 20 to 150° C.,
- are not flammable,
- are water-immiscible.

The term "water-immiscible" is used herein to refer to compounds whose solubility in water at 20° C. is less than 2000 ppm, preferably less than 1500 ppm, even less than 1000 ppm.

In a preferred embodiment the solubility of water in the hydrofluoroether is at most 200 ppm, preferably at most 150 ppm.

For the avoidance of doubts, "flammable", when referred to a liquid, means that said liquid has a flash point of not more than 60° C.

The hydrofluoroether is preferably characterised by a low telogenic activity in the course of the polymerization reaction which is initiated by the perhaloacyl peroxide. The expression "low telogenic activity" is used herein to indicate that the difference between the melt flow index of the polymer prepared using the perhaloacyl peroxide in trichlorotrifluoroethane and the one prepared using the perhaloacyl peroxide in the hydrofluoroether under otherwise identical reaction conditions is no more than 1%, preferably 0%.

Suitable hydrofluoroethers are good solvents for the perhaloacyl peroxide and, preferably, also for the perhaloacyl halide.

In a preferred embodiment the hydrofluoroether is selected from the hydrofluoroethers of formula (IA).

More preferably, the hydrofluoroether is selected from the hydrofluoroethers of formula (IA) wherein: R and R' have the meaning as defined above, with the proviso that at least one of R or R' is a —$C_mF_{2m+1}$ group or a —$C_nF_{2n+1-h}H_h$ group wherein m≥3, preferably m≥4, more preferably 4≤m≤8; n≥3, preferably n≥4, more preferably 4≤n≤8, h<2n+1, and at least one of R or R' is a —$C_nF_{2n+1-h}H_h$ group wherein 1≤n≤3, preferably 1≤n≤2, and h=2n+1.

Non-limiting examples of hydrofluoroethers of formula (IA) are for instance: $C_3F_7OCH_3$, $C_4F_9OCH_3$, $C_6F_{13}OCH_3$, $C_4F_9OC_2H_5$, $C_7F_{15}OC_2H_5$, $CF_3CFHCF_2OCH_3$.

Preferred hydrofluoroethers for use in the inventive process are $C_3F_7OCH_3$, $C_4F_9OCH_3$, $C_6F_{13}OCH_3$, $C_7F_{15}OC_2H_5$.

In a first step of the process, an aqueous phase containing an inorganic peroxide is contacted with a mixture comprising the perhaloacyl halide and the hydrofluoroether. The mixture generally consists of the perhaloacyl halide and the hydrofluoroether.

The mixture may advantageously be a solution of the perhaloacyl halide in the hydrofluoroether.

The expression "inorganic peroxide" is used herein to refer to hydrogen peroxide as well as metal peroxides, such as alkali metal peroxides, e.g. sodium or potassium peroxide. The inorganic peroxide may be dissolved in the aqueous phase. Alternatively, the inorganic peroxide may be formed in situ in the aqueous phase before it is contacted with the perhaloacyl halide. In an embodiment of the process the inorganic peroxide is formed in situ by reaction of an alkali metal salt with hydrogen peroxide.

The inorganic peroxide may be obtained by reaction of an alkali metal carbonate, e.g. $K_2CO_3$ or $Na_2CO_3$, with hydrogen peroxide.

The aqueous phase containing the inorganic peroxide is contacted with the mixture comprising the perhaloacyl halide and the hydrofluoroether.

In a preferred embodiment of the inventive process, the hydrofluoroether is selected among those capable of dissolving the perhaloacyl halide as well as the perhaloacyl peroxide.

The perhaloacyl halide which may be used in the process of the present invention may be a compound of formula (II):

$$C_pX2_{p+1}COY \qquad (II)$$

wherein each X is independently selected from the group consisting of F, Cl, Br, I; Y is selected from Cl, Br, I and p is an integer ≥1, preferably p is an integer 1≤p≤5, more preferably 1≤p≤3, even more preferably p=1. Preferably, in formula (II) each X is independently selected from the group consisting of F and Cl, Y is Cl and 1≤p≤3, more preferably p=1.

Preferred perhaloacyl halides are selected from the group consisting of: trichloroacetyl chloride, dichlorofluoroacetyl chloride, chlorodifluoroacetyl chloride, trifluoroacetyl chloride. Preferably the perhaloacyl halide is trichloroacetyl chloride.

The reaction of the inorganic peroxide with the perhaloacyl halide is typically performed at temperatures between 0° C. and the freezing temperature of the reaction mixture, typically −20° C. Generally, the reaction temperature is in the range of −5 to −20° C.

The perhaloacyl halide is reacted with a sufficient quantity of the inorganic peroxide so that a stoichiometric excess of inorganic peroxide is present during the reaction. Generally, 15 to 35% excess of inorganic peroxide is used. Good results have been obtained using an excess of inorganic peroxide ranging from 20% to 30% with respect to the perhaloacyl halide.

The ratio between the aqueous phase comprising the inorganic peroxide and the hydrofluoroether is not a limiting factor in the process. The ratio between the aqueous phase and the hydrofluoroether by volume may typically be from 2:1 to 1:2, preferably from 2:1 to 1:1.

The contact time for the reaction between the perhaloacyl halide and the inorganic peroxide may be 2 to 60 minutes, preferably 5 to 10 minutes.

The reaction typically proceeds with a yield in the perhaloacyl peroxide of more than 40% by moles.

When the perhaloacyl halide is trichloroacetyl chloride the yield in bis(trichloroacetyl) peroxide is more than 40% by moles, more than 50% by moles, more than 60% by moles, more than 70% by moles, even more than 80% by moles. The yield in bis(trichloroacetyl) peroxide may even be more than 95% by moles.

The process is generally performed in a jacketed hastelloy reactor under stirring and temperature control.

The perhaloacyl peroxide which forms in the course of the reaction is not soluble in the aqueous phase and will accumulate in the hydrofluoroether.

In a preferred embodiment of the process the perhaloacyl peroxide is soluble in the hydrofluoroether and the mixture is a solution.

The mixture comprising the hydrofluoroether and the perhaloacyl peroxide is not miscible with the aqueous phase and a biphasic system will form.

In the final step of the process the aqueous phase is separated from the mixture comprising the hydrofluoroether and the perhaloacyl peroxide.

In addition to the perhaloacyl peroxide the mixture may contain residual amounts of the perhaloacyl halide starting material and traces of water.

Hydrofluoroethers that separate rapidly from the aqueous phase are particularly preferred for increasing the efficiency of the process.

Advantageously the perhaloacyl peroxide is soluble in the hydrofluoroether and a solution is formed at the end of the reaction. The mixture, preferably the solution, of the perhaloacyl peroxide in the hydrofluoroether thus obtained may be used without any further purification as a radical initiator in polymerization reactions.

A second object of the invention is thus a mixture comprising a perhaloacyl peroxide and a hydrofluoroether.

The hydrofluoroether represents the major component of the mixture. Traces of other compounds may be present in the mixture, for instance residual amounts of the perhaloacyl halide or water. Advantageously the amount of water in the mixture is no more than 200 ppm, preferably no more than 150 ppm.

Typically the mixture contains from 0.05 to 0.35 g of perhaloacyl peroxide per cm³ of hydrofluoroether, even from 0.08 to 0.30 g/cm³, preferably from 0.10 to 0.30 g/cm³, more preferably from 0.12 to 0.25 g/cm³.

In a preferred embodiment, the mixture is a solution of a perhaloacyl peroxide in a hydrofluoroether. The term "solution" is used herein to refer to a homogeneous mixture which comprises the perhaloacyl peroxide dissolved in the hydrofluoroether.

The perhaloacyl peroxide is preferably bis(trichloroacetyl) peroxide. The definitions and preferences provided for the hydrofluoroether in connection with the process above apply to the definition of the mixture.

A further object of the invention is a process for the preparation of polymers comprising the use of the mixture, preferably the solution, comprising the perhaloacyl peroxide and a halofluoroether as detailed above.

The mixture is used to provide the radical initiator for the polymerization reaction.

Preferably, the process comprises the step of feeding the mixture into the polymerization reaction. The mixture may be added continuously to the polymerization reaction or intermittently.

The process is preferably a process for the preparation of fluorinated polymers.

A further object of the invention is a process for the preparation of fluorinated polymers which comprises:
contacting an aqueous phase comprising an inorganic peroxide with a mixture of a perhaloacyl halide and a hydrofluoroether,
allowing the inorganic peroxide to react with the perhaloacyl halide to obtain a perhaloacyl peroxide,
separating the aqueous phase from a mixture comprising the perhaloacyl peroxide and the hydrofluoroether, and
adding the mixture comprising the perhaloacyl peroxide and the hydrofluoroether to a reaction mixture comprising at least one fluorinated monomer.

The at least one fluorinated monomer is allowed to react forming a polymer. The expression "at least one fluorinated monomer" is used herein to refer to one type of fluorinated monomer and not a single molecule of the same.

Suitable fluorinated polymers are those comprising recurring units derived from at least one fluorinated monomer. Non limiting examples of suitable fluorinated monomers are:
$C_2$-$C_8$ fluoro- and/or perfluoroolefins, such as tetrafluoroethylene, hexafluoropropylene, pentafluoropropylene, and hexafluoroisobutylene;
$C_2$-$C_8$ hydrogenated fluoroolefins, such as vinyl fluoride, 1,2-difluoroethylene, vinylidene fluoride and trifluoroethylene;
(per)fluoroalkylethylenes of formula $CH_2=CH-R_{f0}$, wherein $R_{f0}$ is a $C_1$-$C_6$ (per)fluoroalkyl or a $C_1$-$C_6$ (per)fluorooxyalkyl having one or more ether groups;
chloro- and/or bromo- and/or iodo-$C_2$-$C_6$ fluoroolefins, like chlorotrifluoroethylene;
fluoroalkylvinylethers of formula $CF_2=CFOR_{f1}$ in which $R_{f1}$ is a $C_1$-$C_6$ fluoro- or perfluoroalkyl, e.g. $-CF_3$, $-C_2F_5$, $-C_3F_7$;
hydrofluoroalkylvinylethers of formula $CH_2=CFOR_{f1}$ in which $R_{f1}$ is a $C_1$-$C_6$ fluoro- or perfluoroalkyl, e.g. $-CF_3$, $-C_2F_5$, $-C_3F_7$;
fluoro-oxyalkylvinylethers of formula $CF_2=CFOX_1$, in which $X_1$ is a $C_1$-$C_{12}$ oxyalkyl, or a $C_1$-$C_{12}$ (per)fluorooxyalkyl having one or more ether groups, like perfluoro-2-propoxy-propyl;
fluoroalkyl-methoxy-vinylethers of formula $CF_2=CFOCF_2OR_{f2}$ in which $R_{f2}$ is a $C_1$-$C_6$ fluoro- or perfluoroalkyl, e.g. $-CF_3$, $-C_2F_5$, $-C_3F_7$ or a $C_1$-$C_6$ (per)fluorooxyalkyl having one or more ether groups, like $-C_2F_5-O-CF_3$;
functional fluoro-alkylvinylethers of formula $CF_2=CFY_0$, in which $Y_0$ is a $C_1$-$C_{12}$ alkyl or (per)fluoroalkyl, or a $C_1$-$C_{12}$ oxyalkyl, or a $C_1$-$C_{12}$ (per)fluorooxyalkyl, said $Y_0$ group having one or more ether groups and $Y_0$ comprising a carboxylic or sulfonic acid group, in its acid, acid halide or salt form;
fluorodioxoles, of formula:

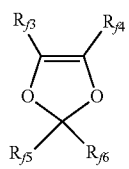

wherein each of $R_{f3}$, $R_{f4}$, $R_{f5}$, $R_{f6}$, equal or different each other, is independently a fluorine atom, a $C_1$-$C_6$ fluoro- or per(halo)fluoroalkyl, optionally comprising one or more oxygen atom, e.g. $-CF_3$, $-C_2F_5$, $-C_3F_7$, $-OCF_3$, $-OCF_2CF_2OCF_3$.

In addition to fluorinated monomers, the fluorinated polymer may comprise hydrogenated monomers such as ethylene and/or propylene.

Advantageously the process is a process for the preparation of polymers comprising recurring units derived from chlorotrifluoroethylene, in particular copolymers of ethylene and chlorotrifluoroethylene.

Polymers comprising recurring units derived from ethylene and chlorotrifluoroethylene typically comprise:
(a) from 10 to 90%, from 30 to 70 by moles of ethylene;
(b) from 90 to 10%, from 70 to 30%, by moles of chlorotrifluoroethylene; and
(c) from 0 to 30%, from 0.1 to 15% by moles, based on the total amount of monomers (a) and (b), of one or more fluorinated and/or hydrogenated comonomer(s).

Non limiting examples of fluorinated comonomers are for instance perfluoroalkylvinylethers, perfluoroalkylethylenes (such as perfluorobutylethylene), perfluorodioxoles, vinylidenefluoride. Among them, the preferred comonomer is perfluoropropylvinylether of formula $CF_2=CFO-C_3F_7$.

Non limiting examples of hydrogenated comonomers, are those having the general formula: $CH_2=CH-(CH_2)_nR^1$ wherein $R^1=OR^2$, or $-(O)_tCO(O)_rR^2$ wherein t and r are integers equal to 0 or 1 and $R^2$ is H or a hydrogenated linear or branched alkyl or cycloalkyl radical having from 1 to 20 carbon atoms, optionally containing heteroatoms and/or chlorine atoms, the heteroatoms preferably being O or N; $R^2$ optionally contains one or more functional groups, preferably selected from OH, COOH, epoxide, ester and ether, $R^2$ may optionally contain double bonds; n is an integer in the range 0-10. Preferably $R^2$ is an alkyl radical having from 1 to 10 carbon atoms containing hydroxyl functional groups and n is an integer in the range 0-5.

Preferred hydrogenated comonomers are selected from the following classes: acrylic monomers having the general formula: $CH_2=CH-CO-O-R^2$, wherein $R^2$ is selected from ethylacrylate, n-butylacrylate, acrylic acid, hydroxyalkylacrylates, such as hydroxyethylacrylate, hydroxypropylacrylate, (hydroxy)ethylhexylacrylate; vinylether monomers having the general formula: $CH_2=CH-O-R^2$, wherein $R^2$ is selected from propylvinylether, cyclohexylvinylether, vinyl 4 hydroxybutylether; vinyl monomers of the carboxylic acid having the general formula: $CH_2=CH-O-CO-R^2$, wherein $R^2$ is selected from vinyl acetate, vinyl propionate, vinyl-2-ethylhexanoate; unsaturated carboxylic acid monomers having the general formula: $CH_2=CH-(CH_2)_n-COOH$, wherein n has the above mentioned meaning, for instance vinylacetic acid.

Any process for the radical polymerization of chlorotrifluoroethylene and ethylene may be used. Processes for the preparation of fluorinated polymers and in particular copolymers of ethylene and chlorotrifluoroethylene are known for instance from U.S. Pat. Nos. 3,624,250, 4,513,129, EP673952 and EP673951.

The present invention will now be described in more details by reference to the following examples, whose purposes are merely illustrative and do not limit the scope of the invention.

Should the disclosure of any of the patents, patent applications, and publications that are incorporated herein by reference conflict with the present description to the extent that it might render a term unclear, the present description shall take precedence.

EXAMPLES

Raw Materials

Novec™ 7100 (supplied from 3M): hydrofluoroether of formula $C_4F_9-O-CH_3$, boiling point 61° C.

Novec™ 7300 (supplied from 3M): hydrofluoroether of formula $C_6F_{13}-O-CH_3$, boiling point 98° C.

Novec™ 7500 (supplied from 3M): hydrofluoroether of formula $C_7F_{15}-O-C_2H_5$, boiling point 128° C.

Trichloroacetyl chloride (TCAC) supplied from HONGDA GROUP LIMITED LLC

Solubility of Trichloroacetyl Chloride

The test was performed by adding 1.38 g of trichloroacetyl chloride to 10 g of hydrofluoroether or 1,1,2-trichloro-1,2,2,trifluoroethane (CFC 113) as the reference at room temperature. The system was stirred for 2 min and then allowed to stand. The system was visually inspected. A transparent solution without any opalescence was considered as a positive indication that a solution was formed. The results are reported in Table 1.

Phase Separation

In a 100 mL separating funnel were introduced 17.9 g of water and 3.6 g of $K_2CO_3$ salt and 8.5 g of the hydrofluoroether. The system was vigorously mixed and then allowed to stand. The time required for a complete separation of the aqueous and hydrofluoroether phases was recorded. The amount of water present in the hydrofluoroether phase was determined by $^1H$ NMR. The results are reported in Table 1.

TABLE 1

|  | $C_4F_9-O-CH_3$ | $C_6F_{13}-O-CH_3$ | $C_7F_{15}-O-C_2H_5$ | CFC 113 |
|---|---|---|---|---|
| TCAC solubility | Transparent No opalescence | Transparent No opalescence | Transparent No opalescence | Transparent No opalescence |
| Phase separation (seconds) | 35 | 27 | 45 | 17 |
| Water (ppm)* | 57 | 94 | 57 | — |

Solutions of the starting material which rapidly phase separate from the aqueous phase were successfully obtained using hydrofluoroethers.

The invention claimed is:

1. A process for the preparation of a perhaloacyl peroxide said process comprising:
   contacting an aqueous phase comprising an inorganic peroxide with a mixture of a perhaloacyl halide and a hydrofluoroether,
   allowing the inorganic peroxide to react with the perhaloacyl halide to obtain a perhaloacyl peroxide, and
   separating the aqueous phase from a mixture comprising the perhaloacyl peroxide and the hydrofluoroether,
   wherein the hydrofluoroether is selected from the hydrofluoroethers of formula (IA):

$$R-O-R' \qquad (IA)$$

with the proviso that at least one of R or R' is a $-C_mF_{2m-1}$ group or a $-C_nF_{2n+1-h}H_h$ group wherein m≥3; n≥3, h<2n+1, and at least one of R or R' is a $-C_nF_{2n+1-h}H_h$ group wherein 1≤n≤3 and h=2n+1.

2. The process of claim 1 wherein the hydrofluoroether has a boiling point in the range from about 20 to about 150° C.

3. The process of claim 1 wherein the perhaloacyl halide is trichloroacetyl chloride.

4. The process of claim 1 wherein the inorganic peroxide is used in an excess from about 20% to about 30% with respect to the perhaloacyl halide.

5. The process of claim 1 comprising allowing the aqueous phase to separate from a mixture comprising the perhaloacyl peroxide and the hydrofluoroether.

6. A mixture comprising a perhaloacyl peroxide and a hydrofluoroether, wherein the mixture contains from 0.05 to 0.35 g of perhaloacyl peroxide per cm³ of hydrofluoroether,
   wherein the hydrofluoroether is selected from the hydrofluoroethers of formula (IA):

$$R-O-R' \qquad (IA)$$

with the proviso that at least one of R or R' is a $-C_mF_{2m-1}$ group or a $-C_nF_{2n+1-h}H_h$ group wherein m≥3; n≥3, h<2n+1, and
   at least one of R or R' is a $-C_nF_{2n+1-h}H_h$ group wherein 1≥n≥3.

7. The mixture of claim 6 wherein the perhaloacyl peroxide is bis(trichloroacetyl) peroxide.

8. A process for the preparation of a fluorinated polymer wherein one or more fluorinated monomers are polymerised in the presence of the mixture of claim 6.

9. The process of claim 8 which comprises the step of feeding a mixture comprising a perhaloacyl peroxide and a hydrofluoroether to a reaction mixture wherein one or more fluorinated monomers are polymerised.

10. The process of claim 8 wherein the fluorinated polymer is a copolymer of ethylene and chlorotrifluoroethylene.

* * * * *